(12) United States Patent
Zucker

(10) Patent No.: US 8,584,852 B2
(45) Date of Patent: Nov. 19, 2013

(54) METAL STENT FOR TREATING LESIONS IN BLOOD VESSELS, COMPRISING A PACKAGING

(75) Inventor: Arik Zucker, Zürich (CH)

(73) Assignee: Qvanteq AG (CH)

( * ) Notice: Subject to any disclaimer, the term of this patent is extended or adjusted under 35 U.S.C. 154(b) by 74 days.

(21) Appl. No.: 13/002,389

(22) PCT Filed: Jun. 9, 2009

(86) PCT No.: PCT/CH2009/000190
§ 371 (c)(1),
(2), (4) Date: Feb. 23, 2011

(87) PCT Pub. No.: WO2010/000080
PCT Pub. Date: Jan. 7, 2010

(65) Prior Publication Data
US 2011/0178590 A1 Jul. 21, 2011

(30) Foreign Application Priority Data
Jul. 4, 2008 (CH) ........................................ 1036/08

(51) Int. Cl.
*B65D 85/00* (2006.01)
*A61F 2/90* (2013.01)
*A61B 19/02* (2006.01)

(52) U.S. Cl.
USPC ............................ 206/438; 206/363; 206/571

(58) Field of Classification Search
USPC ......... 206/570, 571, 363, 364, 438, 439, 806, 206/210, 305; 623/1.15, 1.11, 1.18
See application file for complete search history.

(56) References Cited

U.S. PATENT DOCUMENTS

| | | | | |
|---|---|---|---|---|
| 4,256,225 A | * | 3/1981 | Jackson | 206/303 |
| 5,390,792 A | * | 2/1995 | Van Ness et al. | 206/439 |
| 5,919,145 A | * | 7/1999 | Sahatjian | 600/572 |
| 6,398,031 B1 | * | 6/2002 | Frezza | 206/571 |
| 7,261,205 B2 | * | 8/2007 | Cervantes | 206/364 |

(Continued)

FOREIGN PATENT DOCUMENTS

| | | |
|---|---|---|
| JP | 2005527276 | 9/2005 |
| WO | WO 99/38546 A | 8/1999 |

(Continued)

OTHER PUBLICATIONS

International Search Report dated Aug. 31, 2009, issued in corresponding international application No. PCT/CH2009/000190.

*Primary Examiner* — Steven A. Reynolds
(74) *Attorney, Agent, or Firm* — Ostrolenk Faber LLP

(57) ABSTRACT

The system according to the present disclosure includes a metal stent (3) as a medical implant for treating lesions in blood vessels and a packaging (1) having an inside volume, in which the stent (3) is arranged in a protected manner. The stent (3) has a plurality of webs (33), which produce a tubular shape with each other, and a proximal end (31) and a distal end (32), between which a stent lumen (34) extends. The stent surface (35) has a hydrophilic property. The molecular chemical impurities originating in the atmosphere, primarily hydrocarbon compounds, are significantly reduced on the surface by a treatment, whereby the contact angle as a measure of the hydrophilicity of a water drop present on the surface (35) is reduced in proportion to the contact angle prior to said treatment. The stent (3) is stored in an inert manner in the packaging (1).

7 Claims, 12 Drawing Sheets

(56) References Cited

U.S. PATENT DOCUMENTS

| | | | |
|---|---|---|---|
| 7,353,946 B2 * | 4/2008 | Cervantes | 206/428 |
| 7,694,810 B1 * | 4/2010 | Barry et al. | 206/364 |
| 8,136,659 B2 * | 3/2012 | Salahieh et al. | 206/210 |
| 2002/0130059 A1 * | 9/2002 | Armijo | 206/438 |
| 2003/0060803 A1 * | 3/2003 | McGlinch et al. | 604/533 |
| 2004/0088043 A1 | 5/2004 | Klein | |
| 2005/0109648 A1 * | 5/2005 | Kerzman et al. | 206/364 |
| 2005/0218022 A1 * | 10/2005 | Cervantes | 206/363 |
| 2005/0252805 A1 * | 11/2005 | Cervantes | 206/384 |
| 2005/0268573 A1 * | 12/2005 | Yan | 53/425 |
| 2005/0278012 A1 * | 12/2005 | Vonderwalde | 623/1.11 |
| 2006/0260967 A1 * | 11/2006 | Clarke et al. | 206/438 |
| 2007/0084144 A1 | 4/2007 | Labrecque et al. | |
| 2008/0011640 A1 * | 1/2008 | Cervantes | 206/571 |
| 2008/0086198 A1 * | 4/2008 | Owens et al. | 623/1.39 |
| 2009/0018633 A1 * | 1/2009 | Lindquist et al. | 623/1.11 |
| 2009/0018635 A1 * | 1/2009 | Holman et al. | 623/1.11 |
| 2010/0264050 A1 * | 10/2010 | Clarke et al. | 206/438 |
| 2011/0152995 A1 * | 6/2011 | Mader et al. | 623/1.11 |
| 2012/0239135 A1 * | 9/2012 | Lambert et al. | 623/1.15 |

FOREIGN PATENT DOCUMENTS

| | | |
|---|---|---|
| WO | WO 00/44305 A | 8/2000 |
| WO | WO 03/030957 A | 4/2003 |
| WO | WO 2005/073091 A | 8/2005 |
| WO | WO 2008/021481 A | 2/2008 |

* cited by examiner

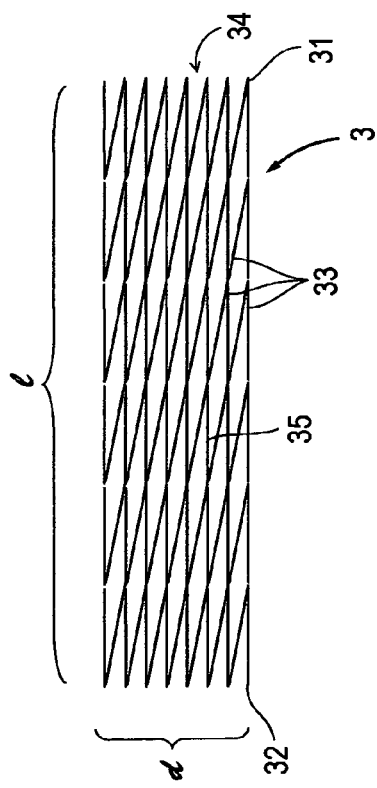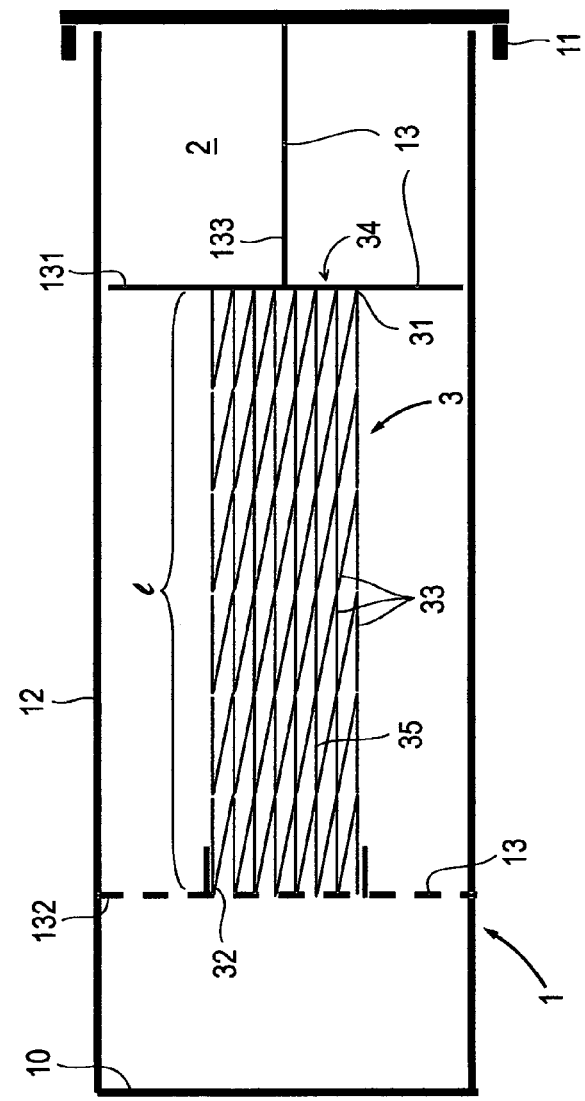

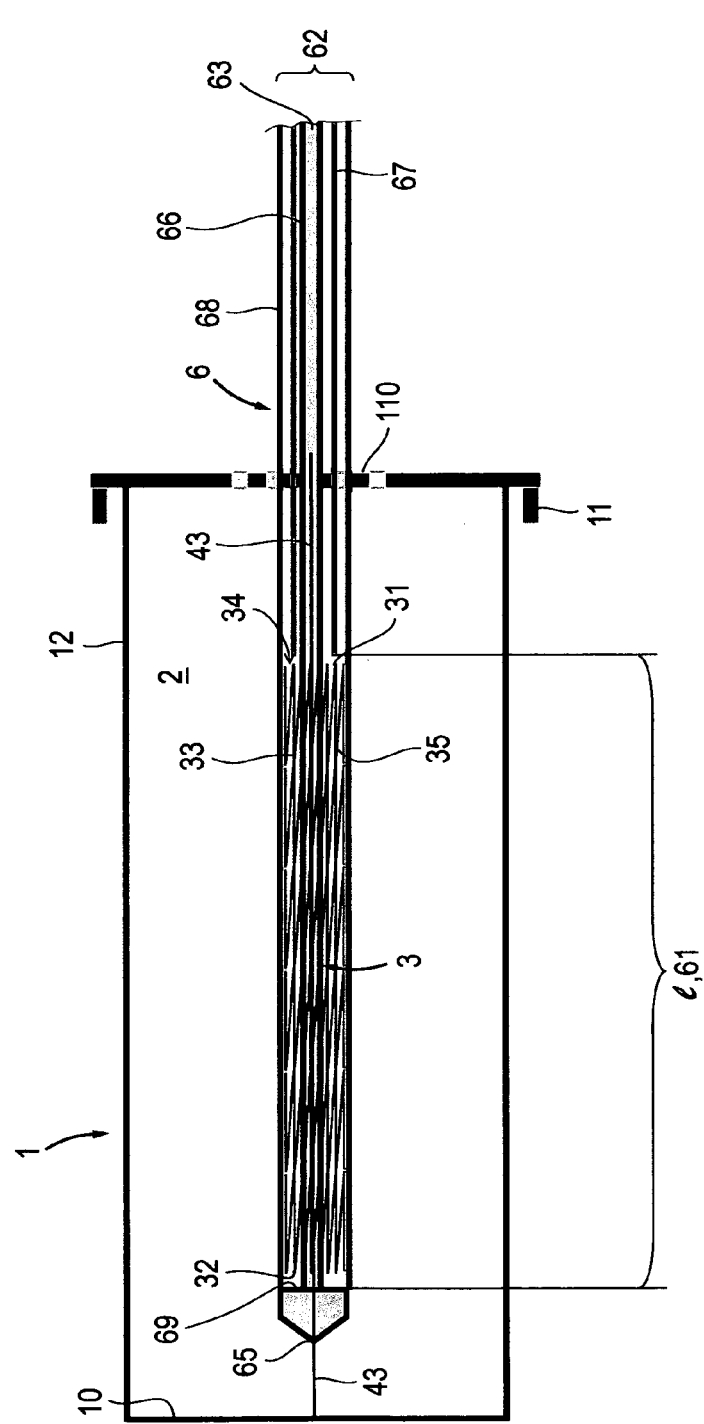

METAL STENT FOR TREATING LESIONS IN BLOOD VESSELS, COMPRISING A PACKAGING

CROSS REFERENCE TO RELATED APPLICATIONS

The present application is a 35 U.S.C. §371 National Phase conversion of PCT/CH2009/000190, filed Jun. 9, 2009, which claims benefit of Swiss Application No.1036/08, filed Jul. 4, 2008, the disclosure of which is incorporated herein by reference. The PCT International Application was published in the German language.

BACKGROUND

1. Field of the Disclosure

The present invention relates to an arrangement, consisting of a metallic stent as a medical implant for treating lesions in blood vessels, and a packaging. The stent is arranged in a protected fashion in the interior volume of the packaging. The stent has a multiplicity of webs, which together form a tubular shape. The stent length and the stent lumen, as a passage, extend between the proximal and the distal end. The stent assumes a corresponding diameter in the dilated or released state. The stent surface is embodied in a hydrophilic fashion to promote hemocompatibility.

A special field of application is the vessel dilation in the field of percutaneous transluminal angioplasty, also including cardiovascular intervention. Such stents are together with a catheter, which is provided specially for this, inserted into the human body through a minimal opening, e.g. by puncturing an artery in the region of the thigh, and are moved up to the lesion, i.e. the vessel restriction to be treated, and are dilated there. Whereas the stent remains in the dilated blood vessel and supports the latter from the inside, the catheter is removed from the body. The flow of blood through the dilated and supported vessel is once again ensured. This process is carried out with the aid of instantaneous X-ray recordings, which on a monitor display both the blood vessels and the instruments inserted into the body.

Another special field of application is the treatment of aneurysms, i.e. dilated blood vessels. In this treatment, a stent graft—consisting of a supporting mesh and a cover—is inserted into the aneurysm in order once again to ensure the conventional blood flow.

2. Related Art

However, the metallic stents implanted into blood vessels harbor certain risks for the patient. Inter alia, thromboses can form at the structures of the stent. Combined with medicaments administered to the patient after the implantation, the occurrences of thromboses in the case of bare metal stents (BMS) could be reduced to less than 1% within the first 10 days. Nevertheless, this is one of the most-feared complications, particularly in the case of the coronary intervention.

A property of the stent that is desired by medical practitioners is the rapid growing in thereof, the so-called reendothelialization. The latter is of the utmost importance for the success of the stent therapy because the cells in this endothelial layer form essential antithrombotic factors. However, as long as the stent has not grown in, and the structures thereof are subjected to the blood flow, it is of the utmost importance to provide an antithrogenic stent surface.

It is well-known that stents with hydrophilic surface properties have a much higher hemocompatibility, i.e. a much lower thrombogenicity. Substances have been applied onto the stent surface by means of coating methods in order to increase the hydrophilicity on the stent surfaces [cf. Seeger J M, Ingegno M D, Bigatan E, Klingman N, Amery D, Widenhouse C, Goldberg E P. Hydrophilic surface modification of metallic endoluminal stents. J Vasc Surg. 1995 September; 22(3):327-36; Lahann J, Klee D, Thelen H, Bienert H, Vorwerk D, Hocker H. Improvement of haemocompatibility of metallic stents by polymer coating. J Mater Sci Mater Med. 1999 July; 10(7):443-8)].

By way of example, possible coating methods include "chemical vapor deposition" (CVD) or "physical vapor deposition" (PVD), by means of which materials, e.g. polymers or metals with defined layer thicknesses, are applied onto the stent surface. It was found that in the case of a polymer-coated BMS, the thrombocyte formation was reduced from 85% (BMS) to 20% (polymer-coated BMS) as a result of the increased hydrophilic properties of the surface.

On the one hand, strong friction forces acting on the stent surface occur during the clinical intervention; on the other hand, high mechanical stresses are generated on the surface of the individual stent webs during the expansion. After implantation, the stent is subjected to a permanent, pulsating load originating from the blood vessel. These high mechanical loads can result in a detachment of the coating, as a result of which there is a significant potential risk of thromboses, microemboli made of coating particles and serious chronic inflammations. Moreover, critical irregularities in the coating were even determined on yet to be implanted stents.

In addition to the mechanical influences, the stent coatings are damaged or broken down by the chemical reactions occurring in the body. Metallic coatings can corrode as soon as the differing electrochemical potential between coating and stent can be equalized via the battery effect by means of an electrolyte, e.g. blood.

Polymer coatings on stents are successively broken down by the body by means of enzymes. This process is often connected with an inflammation of the surrounding vessel cells, which cause undesired cell proliferations, which can lead to a re-narrowing (restenosis) of the blood vessel. Moreover, inflammations can already be caused by the polymer coating itself.

Although such surface modifications promote—as a positive effect—the growing in property of stents, they can however cause clinical complications due to the aforementioned problems. Until now no stent has been available with an optimum, hydrophilic surface that meets both the medical and the mechanical requirements.

SUMMARY

In light of the previous disadvantages in the prior art, the invention is based on the object of providing a stent that has increased hydrophilicity due to surface modification and hence avoids the aforementioned problems. At the same time, a packaging should be provided for storing and transporting the stent provided with the surface modification according to the invention in order to maintain the hydrophilic surface properties of the stent up until its intervention.

In the case of storing initially uncrimped stents in the packaging, a further object consists of proposing means for mounting the stent onto a catheter, wherein the hydrophilic properties of the stent surface must be maintained.

The arrangement according to the invention consists of a metallic stent as a medical implant for treating lesions in blood vessels and a packaging, with an interior volume, in which the stent is arranged in a protected fashion. The stent has a multiplicity of webs, which together form a tubular shape, and a proximal end and a distal end, with a stent lumen extending therebetween. The stent surface has a hydrophilic property. The molecular chemical contaminants originating from the atmosphere, mainly hydrocarbons, are significantly reduced on the surface by a treatment, as a result of which, as a measure of the hydrophilicity, the contact angle of a water droplet situated on the surface is reduced compared to the contact angle before this treatment. The stent is stored in an inert fashion in the packaging in order to prevent natural recontamination from the atmosphere.

The following features relate to special embodiments of the invention: the treatment of the surface for reducing the chemical contamination is carried out as material ablation, namely e.g. by means of sputtering as ion bombardment, electric discharge machining, electrolytic polishing, plasma activation, laser ablation, a mechanically abrasive method, dry etching or wet-chemical etching.

Alternatively, the result of the treatment of the surface for reducing the chemical contamination is an unchanged topography of the surface, wherein the treatment was in this case also carried out e.g. by means of sputtering as ion bombardment, electric discharge machining, electrolytic polishing, plasma activation, laser ablation, a mechanically abrasive method, dry etching or wet-chemical etching. A treatment that does not ablate material, e.g. by means of ultrasound, UV light or ozone, or a combination treatment formed therefrom, can likewise lead to an unchanged surface topography. An etching medium that does not corrode the stent material itself is equally suitable for this.

The entire content of the packaging is inert and the packaging contains an inert filling.

A catheter is arranged in the packaging and a stent is mounted on said catheter, wherein a balloon catheter or a tube catheter is assigned in a complementary fashion to a balloon-expanding or a self-expanding stent.

The packaging consists of a container with a base and a cover. The base and/or the cover can be removed. The base and/or the cover has/have an access to be opened such that the stent can be removed from the packaging or the stent mounted on a catheter can be removed from the packaging together with the catheter.

The catheter has a tip at its distal end, and the proximal end of the shaft of the catheter opposite the tip protrudes through the access to outside of the packaging.

There is a passage in the base or in the cover for allowing a shaft to pass, which shaft leads to the jaws of an integrated crimping apparatus toward the inside, into the packaging, and leads to an activator for actuating the crimping apparatus toward the outside. The access to be opened is opposite the passage in the cover or in the base, which access serves to let a catheter pass. A guide mandrel extends through the crimping apparatus in the axial direction and it is used for stabilization and positioning purposes after it has been completely inserted into a guide wire lumen of the catheter. The access to be opened is advantageously made of e.g. a penetrable seal or a perforatable material.

Support elements for fixing the stent and/or the catheter and/or the crimping apparatus extend within the packaging.

The stent is embodied with a cover to form a stent graft for the application in the case of aneurysms.

BRIEF DESCRIPTION OF THE DRAWINGS

In the figures:

FIG. 1A shows a balloon-expanding or self-expanding stent in the uncrimped state;

FIG. 1B shows a packaging with a stent as per FIG. 1A stored therein in an inert filling;

FIG. 6 shows a packaging with a self-expanding stent stored therein in an inert filling, mounted on a catheter and in the crimped state.

DETAILED DESCRIPTION OF THE EMBODIMENTS

Figure 2A:
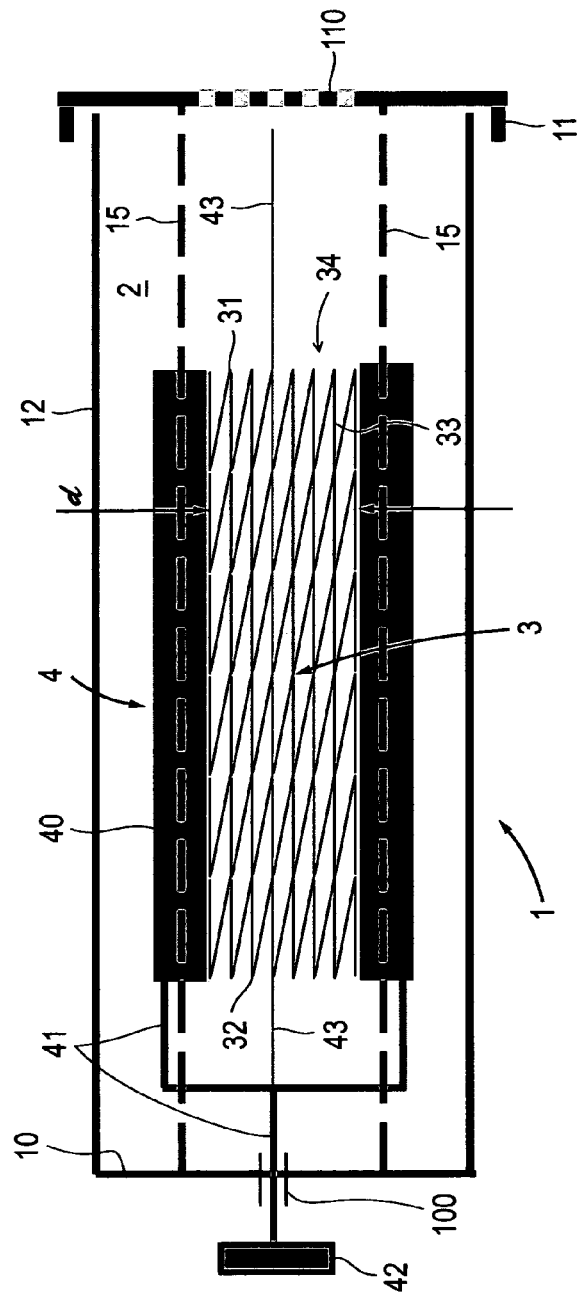
FIG. 2A shows the arrangement as per FIG. 1B with access into the packaging and an open crimping apparatus integrated therein.

In the following text, and with reference to the attached drawings, there is a detailed description of the arrangement according to the invention, which consists of a metallic stent—as a medical implant for treating lesions in blood vessels—and a packaging with an interior volume, in which the stent is arranged in a protected fashion.

The following statement holds true for the entire subsequent description: If reference signs are contained in a figure for the purpose of unambiguity in the drawing but not mentioned in the directly associated text of the description, reference is made to the description thereof in the preceding or subsequent descriptions of the figures. In the interest of clarity, repeated designation of components in further figures is generally dispensed with, provided it is clear from the drawing that these are "recurrent" components.

FIG. 1A

The illustrated stent 3 has a conventional material configuration and structural design; it could be balloon-expanding or self-expanding. The stent 3 is of length 1, which extends between the proximal end 31 and the distal end 32. In the non-crimped state, the stent 3 assumes the diameter d, and so the webs 33 with the surface 35 are spaced from one another in a spacious and grid-shaped fashion. The stent lumen 34, in principle of cylindrical design, runs through the tubular stent 3.

FIG. 1B

The stent 3 is in a packaging 1 and in the process is fixed by a support 13 arranged in the packaging 1, which support first of all comprises a first support element 131, against which the proximal end 31 butts. The distal end 32 is held by the second support element 132. The packaging 1 first of all comprises the container 12 with the base 10 and is sealed by the cover 11 on the end opposite the base 10. The first support element 131 extends like a separation wall over the cross-sectional area of the container 12 and faces the cover 11, wherein a third support element 133 connects the cover 11 with the first support element 131 in the axial direction. The second support element 132 likewise extends like a separation wall over the cross-sectional area of the container 12, but it faces the base 10. There is an inert filling 2 in the packaging 1 and it protects the surface 35 of the stent 3. The inner faces of the packaging 1 facing the stent 3 are inert.

The preceding treatment of the surface 35 increased the hydrophilic property thereof. The molecular chemical contaminants on the surface 35 originating from the atmosphere—mainly hydrocarbons—were significantly reduced, as a result of which, as a measure of the hydrophilicity, the contact angle of a water droplet situated on the surface 35 is reduced.

The chemical contaminants on the surface 35 can preferably be reduced by material ablation. Sputtering as ion bombardment, electric discharge machining, electrolytic polishing, plasma activation, laser ablation, mechanically abrasive methods, dry etching or wet-chemical etching lends itself for this purpose. Alternatively, the reduction in the chemical contaminants on the surface 35 is achieved by a treatment that does not change the topography of the surface 35. Treatment by means of ultrasound, UV light or ozone, or a combination treatment formed therefrom, can be considered for this. An etching medium that does not corrode the stent material itself is equally suitable for the treatment, for example an acid treatment of the surface. 95%-97% sulfuric acid on a cobalt-chromium alloy has proven its worth.

Figure 2C:
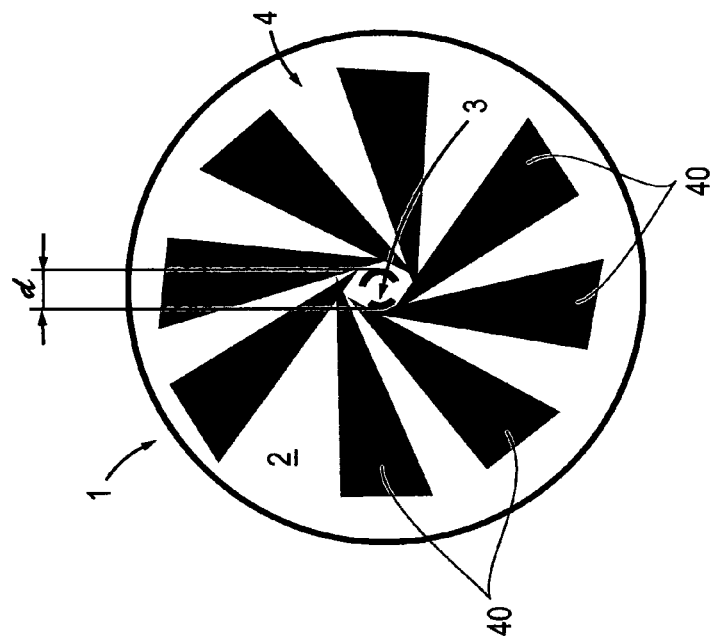
FIG. 2C shows the crimping apparatus as per FIG. 2B in the closed state.
Figure 2B:
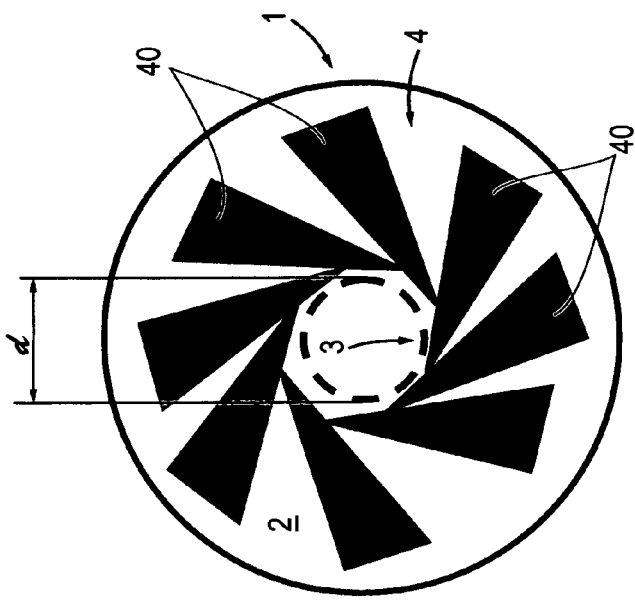
FIG. 2B shows the crimping apparatus from FIG. 2A in the opened state.

FIGS. 2A to 2C

This group of figures schematically illustrates the function of a crimping apparatus 4 arranged in the packaging 1. At first, the crimping apparatus 4 is open, and so the jaws 40 thereof assume a dilated position and thereby encompass the expanded stent 3 situated in the packaging 1 (see FIGS. 2A, 2B). The stent 3 is pretreated as already explained with reference to FIG. 1B. The packaging 1 in turn contains the inert filling 2 and the inner wall of the packaging is inert. The jaws 40 are seated on a shaft 41, which, in the axial direction, leads outward through a passage 100 in the base 10 to an actuatable activator 42. Axes 15, which extend axially between the base 10 and the cover 11, pass through the container 12. A guide mandrel 43 belonging to the crimping apparatus 4 runs centrally through the container 12, which mandrel ends within the container 12 in front of an access 110, which is on the cover 11 and can be perforated. If the crimping apparatus 4 is closed, the jaws 40 are narrowed in the radial direction, and so the stent 3 has a compressed diameter d (see FIG. 2C).

Figure 3A:
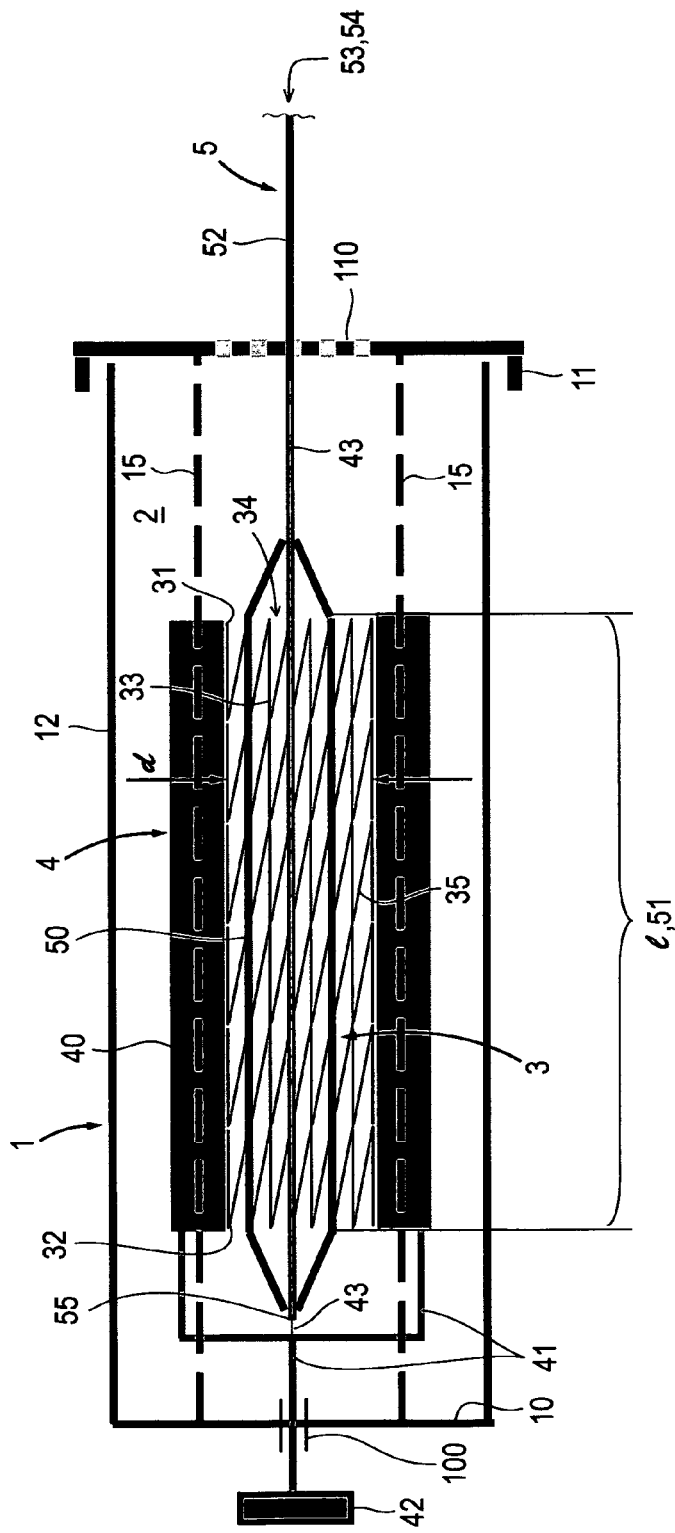
FIG. 3A shows the arrangement as per FIG. 2A with a balloon-expanding stent, a positioned dilation catheter and an opened crimping apparatus.
Figure 3B:
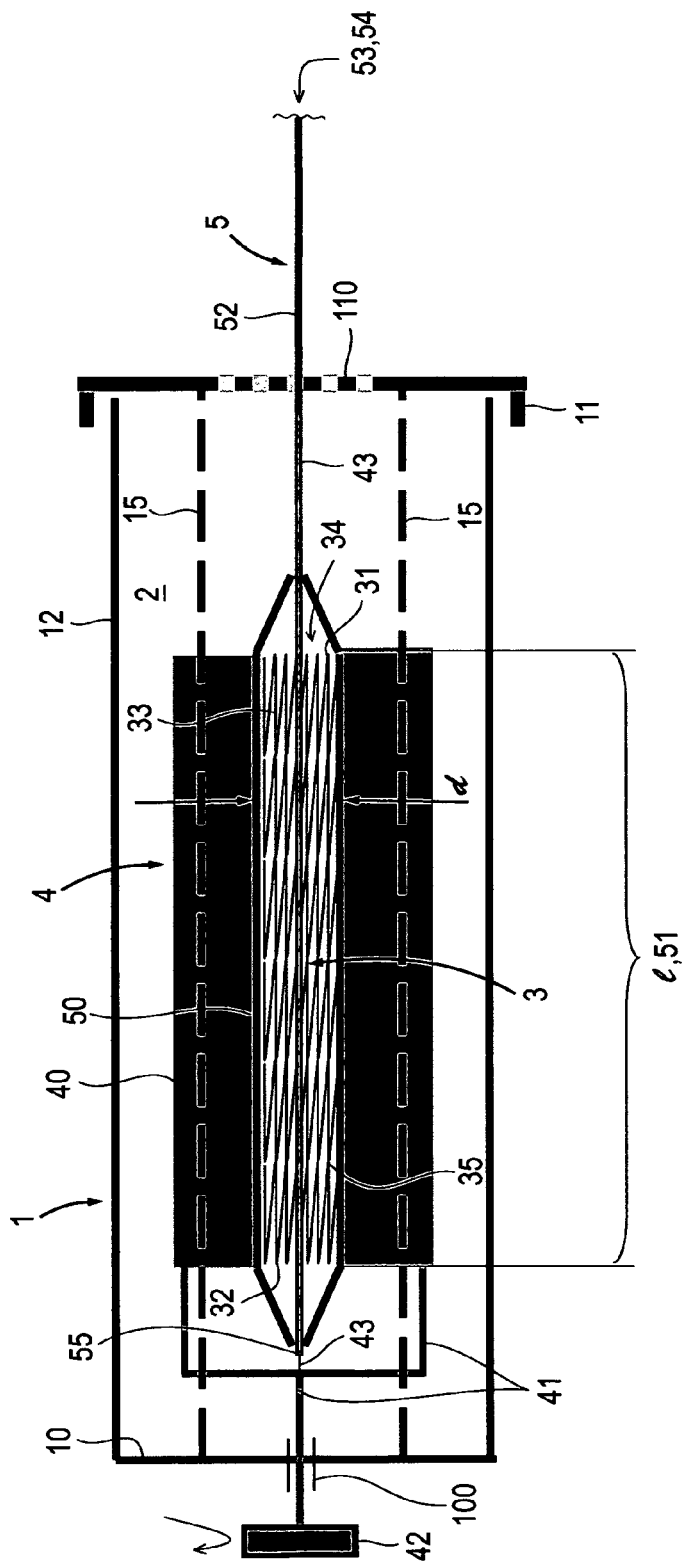
FIG. 3B shows the arrangement as per FIG. 3A with a closed crimping apparatus.
Figure 4:
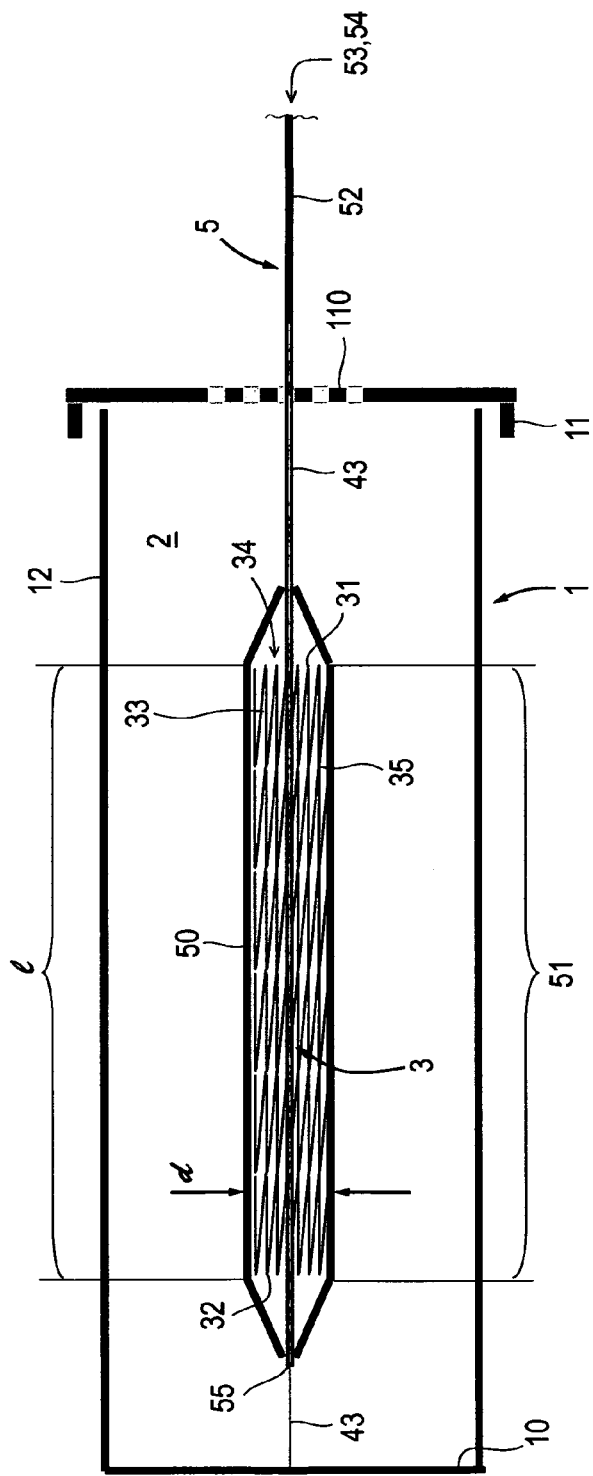
FIG. 4 shows a packaging with a balloon-expanding stent stored therein in an inert filling, on a dilation catheter and in the crimped state.

FIGS. 3A and 3B

This pair of figures is based on the arrangement as per FIG. 2A, wherein the utilized stent 3 is balloon-expanding and was subjected to a pretreatment in order to increase the hydrophilicity of the surface 35, as explained with reference to FIG. 1B. Once again, an inert filling in the packaging 1 and an inert property of the inner wall thereof are assumed. The jaws 40 of the crimping apparatus 4 are open at first (see FIG. 3A). The balloon 50 of the catheter 5 arranged on the shaft 52 has been inserted into the stent lumen 34, tip 55 first, through the access 110, which is in the cover 11 and can be perforated. In the process, the guide mandrel 43 has penetrated the guide wire lumen 53 in the shaft 52. The shaft 52 furthermore has the channel-like dilation lumen 54, by means of which the balloon is brought to expand by being filled up on the inside—e.g. by means of physiological saline—from an external source during the operation and thus dilates the stent 3 from the inside. The stent region 51 of the balloon 50 is in the stent lumen 34, and so the stent region 51 at least in principle passes through the entire length 1 of the stent, while the tapering ends of the balloon 50 protrude from the proximal end 31 and the distal end 32 of the stent 3.

After actuating the activator 42 by rotating it, e.g. manually, the crimping apparatus 4 reaches the closed state, and so the diameter d of the stent 3 is pressed together (see FIG. 3B). In the case of the now narrowed stent diameter d and the compressed jaws 40 of the crimping apparatus 4, the stent region 51 of the balloon 50 remains in an unchanged axial position within the stent lumen 34.

FIG. 4

As an alternative to the design as per the preceding figures, where a crimping apparatus 4 is integrated in the packaging 1, here the packaging 1 now contains a balloon-expanding stent 3 in the crimped state on the balloon 50 of a dilation catheter 5. Here, the stent diameter d is narrowed and the webs 33 are pushed against one another. The stent region 51 of the balloon 50 once again extends over the length 1 of the stent, at least in principle. The guide mandrel 43, which extends from the base 10, has penetrated the guide wire lumen 53 of the shaft 52. The tip 55 comes to rest near the base 10. The interior of the packaging 1 is provided with the inert filling 2 that protects the surface 35 of the stent 3, which is pretreated as per the description in respect of FIG. 1B. Furthermore, the assumption is made that the inner wall of the packaging 1 is inert. The dilation catheter 5 including crimped stent 3 and balloon 50 can be pulled out of the packaging 1 through the access 110, which is in the cover 11 and can be perforated.

FIGS. 5A to 5E

In this sequence of figures, the packaging 1 has an integrated crimping apparatus 4 and use is made of a self-expanding stent 3 and a tube catheter 6. The crimping apparatus 4 once again includes the shaft 41, which extends to the activator 42 through the passage 100 in the base 10, and the guide mandrel 43 passing axially through the packaging 1. The packaging 1 contains the inert filling 2 and the packaging inner wall is inert. The axes 15 again lie within the packaging 1. The surface 35 of the stent 3 has been pretreated in order to increase the hydrophilicity, as explained with reference to FIG. 1B.

Figure 5A:
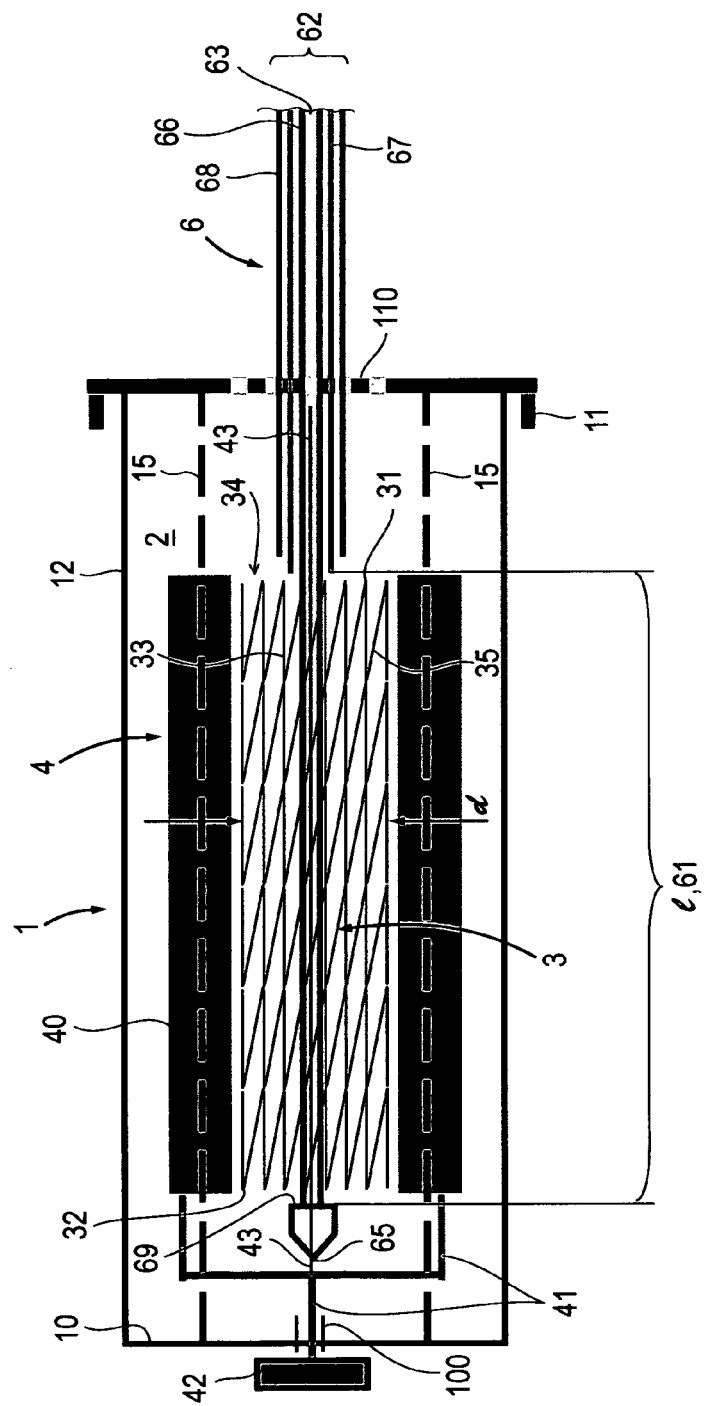
FIG. 5A shows a packaging with an access and with an uncrimped self-expanding stent stored therein in an inert filling, a positioned catheter, and an opened crimping apparatus.

FIG. 5A (Initial Situation)

The jaws 40 of the crimping apparatus 4 are open; it follows that the stent 3 is in the uncrimped state and the inner tubing 66 of the tube catheter 6 has been pushed through the access 110, which is in the cover 11 and can be perforated, and through the stent lumen 34 to the extent that the tip 65 protrudes from the stent 3 and faces the base 10. The guide mandrel 43 has penetrated the guide wire lumen 63 of the shaft 62 in the axial direction. The support tubing 67 and the outer tubing 68 have likewise been pushed through the access 110, which can be perforated, but the free ends thereof are in front of the proximal end 31 of the stent 3. The stent region 61, which can hold the length 1 of the stent, extends between the free end of the support tubing 67 and the stop 69 at the tip 65.

Figure 5B:
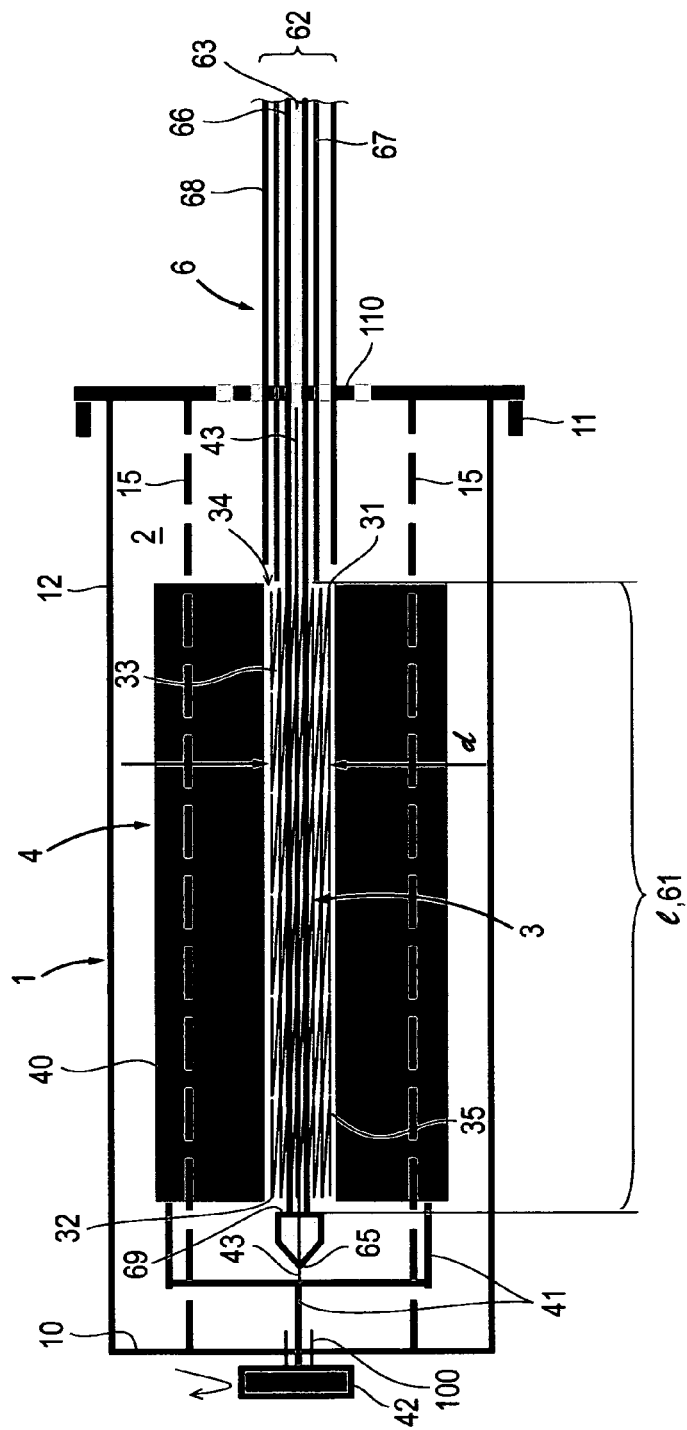
FIG. 5B shows the arrangement as per FIG. 5A, in the crimped state, with a closed crimping apparatus.

FIG. 5B (1st Continuation Step)

The jaws 40 of the crimping apparatus 4 have now been closed, and so the webs 33 of the stent 3 lie pushed together and the stent diameter d is narrowed. The crimping apparatus 4 was actuated by rotating the activator 42. The tube catheter 6, comprising the tip 65, the inner tubing 66, the support tubing 67, and the outer tubing 68, remains in the same position. The stent 3 is cooled in the crimped state in order to disable the self-expanding property when the temperature drops below a defined threshold.

Figure 5C:
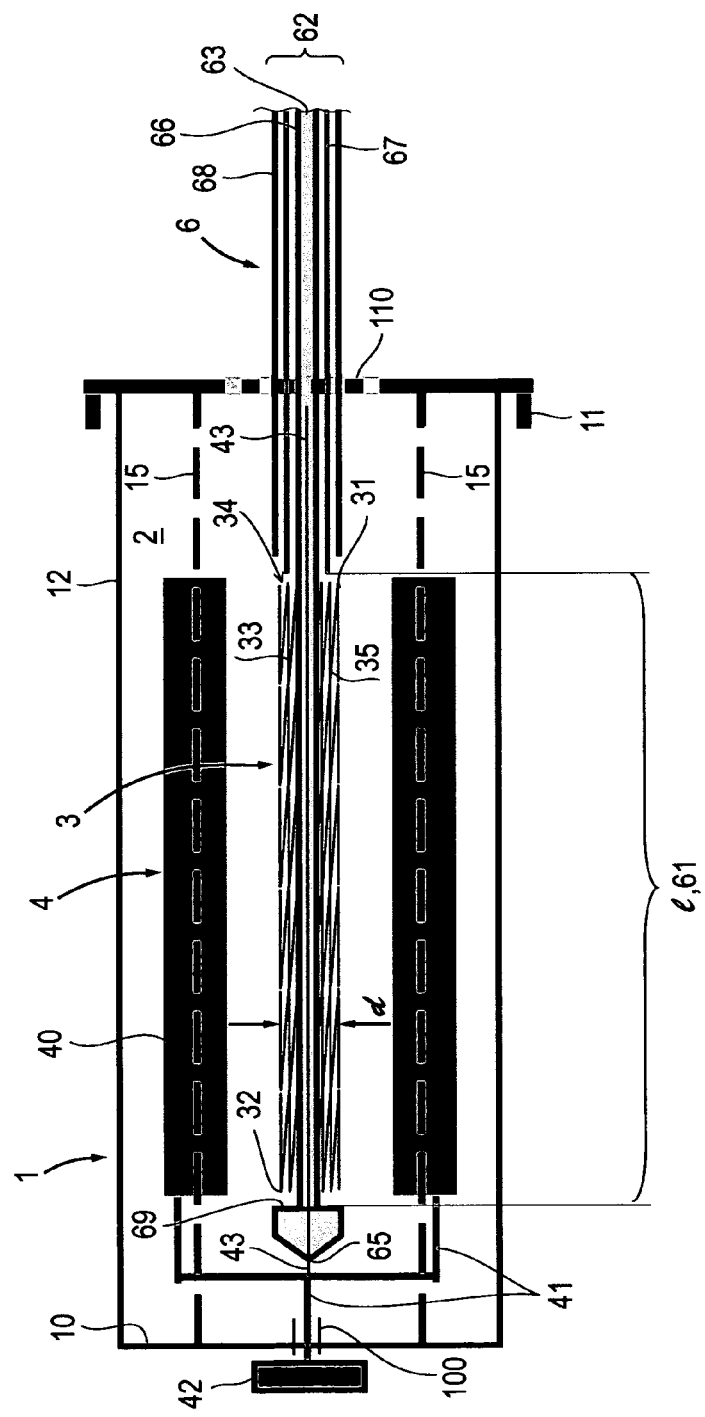
FIG. 5C shows the arrangement as per FIG. 5B with an opened crimping apparatus.

FIG. 5C (2nd Continuation Step)

The jaws 40 of the crimping apparatus 4 are opened, with the self-expanding stent 3 remaining in the crimped state with the narrowed stent diameter d and the compacted webs 33 as a result of the prior temperature drop.

Figure 5D:
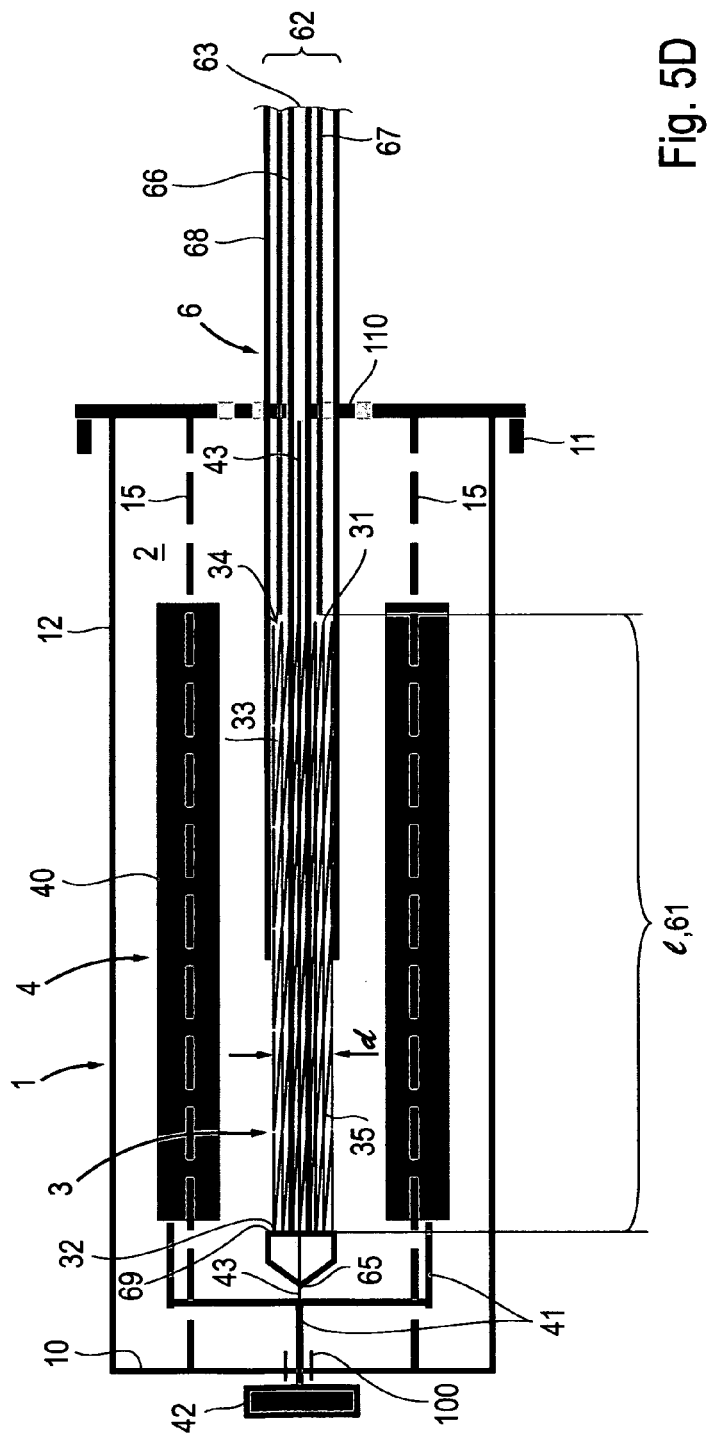
FIG. 5D shows the arrangement as per FIG. 5C, with an external tubing of the catheter that has in part been pushed over the crimped stent.

FIG. 5D (3rd Continuation Step)

The stent 3 remaining in the crimped state with the narrowed stent diameter d allows successive pushing of the outer tubing 68 onto the stent 3 in the direction of the distal end 32 from the proximal end 31. The support tubing 67 and the tip 65 arranged on the inner tubing 66 remain in the same position. The advance of the outer tubing 68 also moves the stent 3 in the same direction, with the stop 69 preventing the further advance of the stent 3.

Figure 5E:
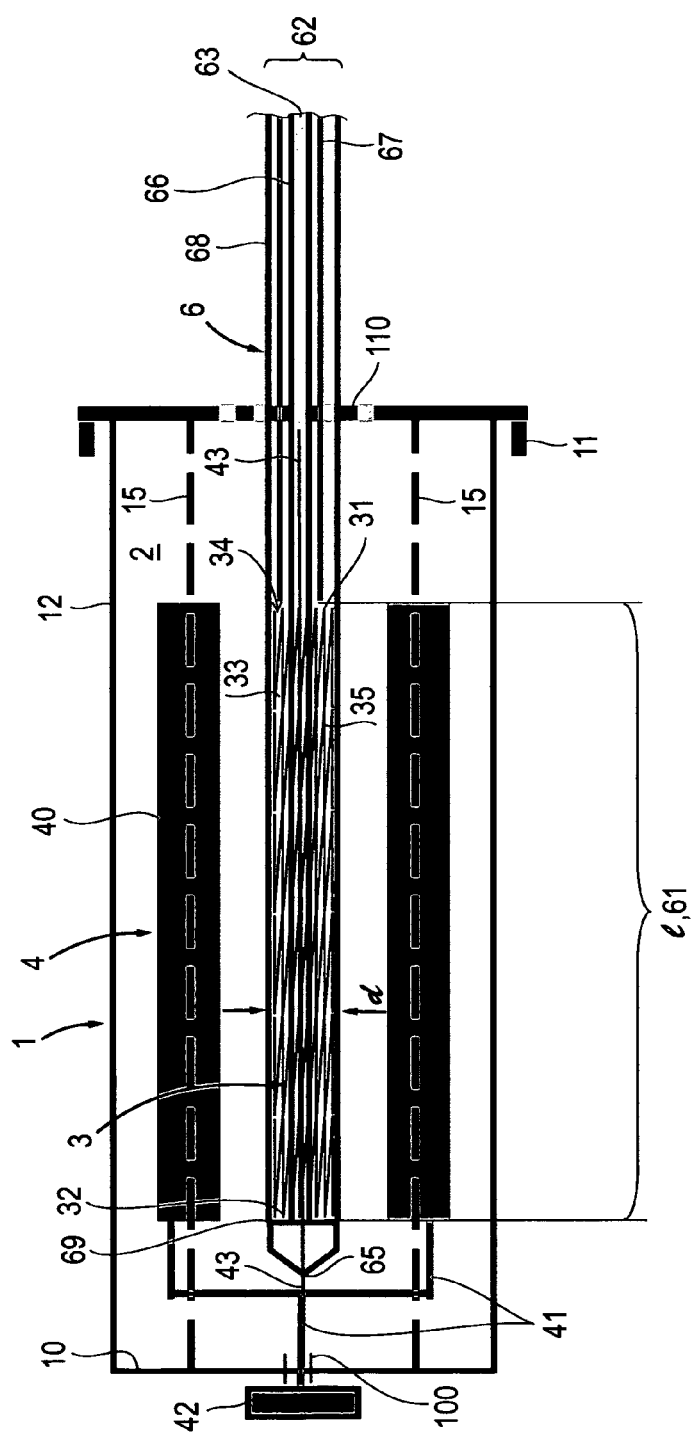
FIG. 5E shows the arrangement as per FIG. 5D with an external tubing of the catheter completely pushed over the crimped stent.

FIG. 5E (4th Continuation Step)

The outer tubing 68 has been pushed so far over the crimped stent 3 that it meets the stop 69 behind the tip 65 and it follows that it now covers the entire stent region 61. In this state, the tube catheter 6 with the crimped stent 3 accommodated therein is pulled out of the packaging 1 through the access 110, which can be perforated, in order to apply the stent 3, which has been prepared as detailed above, to the patient at the predetermined site in the body.

FIG. 6

As an alternative to the design as per the preceding sequence of FIGS. 5A to 5E, where a crimping apparatus 4 is integrated in the packaging 1, the self-expanding stent 3 has now been crimped outside of the packaging 1 and mounted on the tube catheter 6 and inserted into the packaging 1 such that there is no need for a crimping apparatus 4 belonging to the packaging 1. The guide mandrel 43 has been inserted into the guide wire lumen 63. The shaft 62 with outer tubing 68, support tubing 67 and inner tubing 66 protrude outward through the access 110, which is in the cover 11 and can be perforated. The outer tubing 68 butts against the stop 69 of the tip 65 and thus spreads over the entire stent region 61. The free end of the support tubing 67 is in front of the proximal end 31 of the stent 3. Further handling is brought about as in connection with FIG. 5E.

The assumption is made that the stent 3 utilized in this case has had the same pretreatment as in all preceding exemplary embodiments as per FIGS. 1B to 5E and the packaging 1 contains an inert filling 2 and the packaging inner wall is inert.

What is claimed is:

1. An arrangement comprising:
    a bare metal stent used as a medical implant for treating lesions in blood vessels; and
    a packaging with an interior volume in which the stent is arranged in an inert fashion in the packaging in order to prevent natural recontamination from the atmosphere;
    the stent comprising:
        a multiplicity of webs, which together form a tubular shape;
        a proximal end and a distal end, with a stent lumen extending therebetween; and
        a bare metal surface with a hydrophilic property,
        wherein molecular chemical contaminants originating from the atmosphere, mainly hydrocarbons, are significantly reduced on the bare metal surface by a treatment, as a result of which, as a measure of the hydrophilicity, the contact angle of a water droplet situated on the bare metal surface is reduced compared to the contact angle before this treatment; and
    the packaging including:
        a container with a base and a cover; wherein
        at least one of the base or the cover includes an access that is opened such that the stent is removable from the packaging.

2. The arrangement as claimed in claim 1, further comprising:
    a catheter arranged in the packaging with the stent mounted on the catheter, wherein the catheter is one of a balloon catheter and a tube catheter.

3. The arrangement as claimed in claim 2, wherein the catheter includes a tip at a distal end thereof and the proximal end of a shaft of the catheter opposite thereto protrudes through the access outside of the packaging.

4. The arrangement as in claim 1, wherein the access is made of at least one of one of a penetrable seal and perforable material.

5. The arrangement as claimed in claim 2, further comprising:
    a passage formed in at least one of the base or the cover for allowing a shaft to pass, wherein the shaft leads to jaws of an integrated crimping apparatus toward the inside, into the packaging, and leads to an activator for actuating the crimping apparatus toward the outside, the access is positioned opposite the passage in the cover or in the base and allows a catheter pass; and
    a guide mandrel extending through the crimping apparatus in the axial direction used for stabilization and positioning purposes after it has been completely inserted into a guide wire lumen of the catheter.

6. The arrangement according to claim 5, further comprising support elements configured to fix at least one of the stent, the catheter and the crimping apparatus and positioned in the packaging.

7. The arrangement of claim 1, wherein the packaging material is inert and the packing is filled with an inert filling.

* * * * *

UNITED STATES PATENT AND TRADEMARK OFFICE
CERTIFICATE OF CORRECTION

PATENT NO. : 8,584,852 B2  Page 1 of 1
APPLICATION NO. : 13/002389
DATED : November 19, 2013
INVENTOR(S) : Arik Zucker It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

Signed and Sealed this
Twenty-second Day of September, 2015

Michelle K. Lee
*Director of the United States Patent and Trademark Office*